(12) United States Patent
Lopez

(10) Patent No.: US 6,734,669 B2
(45) Date of Patent: May 11, 2004

(54) DIGITAL DEMODULATION OF AN EDDY CURRENT SIGNAL

(75) Inventor: Estell Lopez, Issaquah, WA (US)

(73) Assignee: Zetec, Inc, Issaquah, WA (US)

( * ) Notice: Subject to any disclaimer, the term of this patent is extended or adjusted under 35 U.S.C. 154(b) by 89 days.

(21) Appl. No.: 10/167,166

(22) Filed: Jun. 11, 2002

(65) Prior Publication Data

US 2003/0227288 A1 Dec. 11, 2003

(51) Int. Cl.[7] .............................................. G01N 27/82
(52) U.S. Cl. ...................................... 324/238; 324/242
(58) Field of Search ........................ 324/228, 234–243, 324/226

(56) References Cited

U.S. PATENT DOCUMENTS

| 3,576,489 A | * | 4/1971 | Law et al. ................. 324/233 |
| 4,849,693 A | * | 7/1989 | Prince et al. .............. 324/225 |
| 5,508,610 A | * | 4/1996 | Feeney et al. ............. 324/233 |
| 2002/0163333 A1 | * | 11/2002 | Schicker et al. .......... 324/242 |

* cited by examiner

Primary Examiner—Jay Patidar
(74) Attorney, Agent, or Firm—David L. Tingey

(57) ABSTRACT

A digital synthesizer generates an electrical digital carrier that drives probe coil to generate an electromagnetic wave propagated into a test material proximate the probe coil. A return electromagnetic wave generated by eddy currents in the material includes signatures of material defects modulated on the return carrier electromagnetic wave. The return wave is detected by one or more probe coils, amplified, converted from an analog signal to a digital signal and then digitally mixed with digital sine and cosine functions also generated by the digital synthesizer to yield sum and difference values, mathematically expressing various eddy current signals received by the probe in a complete set of orthogonal functions. A low pass filter then removes all but the difference values. A direct current reference component is subtracted from the mixed digital signal, which translates the signal to center about a zero axis for ease of display and analysis.

17 Claims, 2 Drawing Sheets

DIGITAL DEMODULATION OF AN EDDY CURRENT SIGNAL

BACKGROUND

1. Field of Technology

This invention relates to eddy current signal processing, and more particularly to extraction of an eddy current signal by digitally demodulating a carrier signal returned from an eddy current probe.

2. Prior Art

When an eddy current probe is in the vicinity of a flaw in a material, such as a hole or a crack, the flaw will modulate a carrier signal introduced into the material from an alternating current in a coil in the eddy current probe.

It is well known to extract the signal through analog signal processing. Generally, an oscillator generates a carrier signal and corresponding sine and cosine waves, which are then low-pass filtered. The carrier signal drives a probe coil that generates an electromagnetic field that penetrates into a nearby material. An eddy current is generated in the material, which generates its own electromagnetic field that is detected by the probe coil. When the material is without flaws, the two electromagnetic fields are largely out of phase and the fields partially cancel. However, when a flaw exists in the material, the amplitude and phase of the second field are modified and a small detectable signal results, modulated on the return carrier signal. The signal is amplified and then mixed, or multiplied, with the sine and cosine waves and again low-pass filtered. That is, the signal is mathematically factored into components of a complete set of orthogonal functions, which are represented by the sine and cosine functions. The signals out of the multipliers contain sum and difference products of the two frequencies that contain the amplitude and phase information of the flaw and of the harmonics of those frequencies. The low-pass filters reject all but the difference frequencies and any low-frequency harmonic products.

A programmable summer and a programmable amplifier then shift and scale the eddy current signals so that they optimize the input range of the analog to digital converter. A multiplexer than connects one signal component at a time to the computer through an analog to digital converter. The computer controls the frequency setting, the programmable summer, and the programmable amplifier. It also dictates the rate at which the analog to digital converter digitizes the eddy current signals.

Recent availability of digital components allows digital circuitry to perform many of the above functions digitally, yielding several advantages over analog processing. Digital processing reduces the number of components that must be installed on a circuit board, which may then be reduced in size. Fewer components may also lead to lower manufacturing costs and fewer manufacturing defects. Digital processing is also not concerned with variations caused by component tolerances or drift due to temperature and age, both of which are concerns for the analog method. It is also likely that the digital method will consume less power, especially as advances in CMOS continue to decrease the power consumption of digital circuits. These advantages of digital processing outweigh the disadvantage that digital circuitry is more complex, which is offset in that the digital circuitry still costs less than the analog multipliers.

SUMMARY

A digital synthesizer generates an electrical digital carrier that drives probe coil to generate an electromagnetic wave propagated into a test material proximate the probe coil. A return electromagnetic wave generated by eddy currents in the material includes signatures of material defects modulated on the return carrier electromagnetic wave. The return wave is detected by one or more probe coils, amplified, converted from an analog signal to a digital signal and then digitally mixed with digital sine and cosine functions also generated by the digital synthesizer to yield sum and difference values, mathematically expressing various eddy current signals received by the probe in a complete set of orthogonal functions. A low pass filter then removes all but the difference values. A direct current reference component is subtracted from the mixed digital signal, which translates the signal to center about a zero axis for ease of display and analysis.

DETAILED DESCRIPTION OF THE PREFERRED EMBODIMENT

Figure 1:
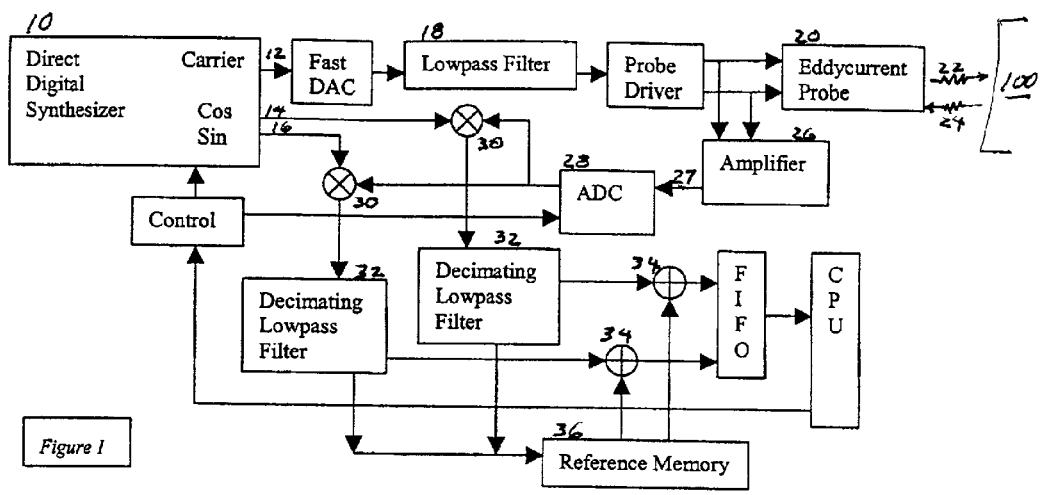
FIG. 1 is a block diagram of a circuit for digital signal processing of an eddy current signal.
Figure 2:
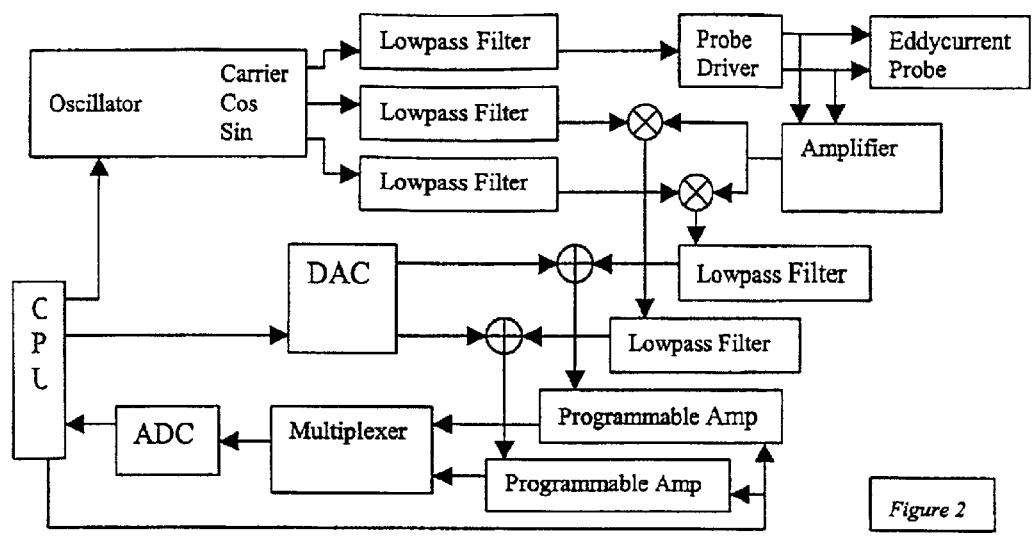
FIG. 2 is a block diagram of a circuit for analog signal processing of an eddy current signal, for comparison with digital signal processing of FIG. 1.

The present invention comprises a digital eddy current signal processing method functionally similar to analog signal processing. A digital synthesizer 10 produces three digital sine waves 12, 14, and 16 that all have the same frequency, two of which are separated in phase by ninety degrees, establishing sine and cosine waves 14 and 16. The third wave 12 is the carrier sine wave, which has variable amplitude and phase relative to the sine and cosine waves. Where a comparable oscillator of an analog method includes three high-speed digital-to-analog converters to generate the sine waves, in the digital method, only one is needed to generate a single wave (the carrier), typically using a digital phase accumulator and sine and cosine look-up tables. Each of the three waves is then derived from those tables.

The carrier signal 12 passes through a low-pass filter 18 and driven to the eddy current probe 20, which transmits an electromagnetic wave 22 into material 100 proximate the probe 20, generating eddy currents in the material. Defects in the material cause amplitude and phase differences in a return electromagnetic wave generated by the eddy currents. The phase differences, or equivalently frequency changes, constitute a signature of the defects as a modulation of the return wave. The probe detects the return electromagnetic wave 24 through one or more probe coils. An analog amplifier 26 amplifies the return signal from the probe. The analog amplifier may include a selectable gain value to optimize the input range of the analog-to-digital converter, increasing the gain of the amplifier to detect small flaws.

After amplification, an analog-to-digital converter 28 digitizes the modulated carrier signal 27, the digitizing rate determined by digital control logic. If the signal is digitized prior to amplification, the amplifier is also digital.

A digital mixer 30 demodulates the signal from the carrier signal 12. Digital sine and cosine waves 14 and 16 from the synthesizer 10 mathematically multiply digital input samples of the carrier signal 27 from the analog to digital converter 28 in the digital mixer 30. Multiplication by the sine and cosine waves creates in-phase and quadrature outputs useful for maintaining amplitude and phase information contained in the modulated input carrier signal 27 and a single-sideband complex translation of the real part of the input carrier wave 27. Unlike analog mixers, which also generate many unwanted mixer products, the digital mixer produces only sum and difference frequency signals without harmonics of the two signals.

Decimating low-pass filters 32 then reject all but the difference frequencies, which together comprise the eddy current signal, effectively translating frequencies in the input signal to lower frequencies. With higher frequencies no longer present, the signal can be represented by a much smaller data sample in keeping with the Nyquist sampling theorem (any signal can be represented by discrete samples if the sampling rate is at least twice the bandwidth of the signal).

Following the decimating low-pass filters 32 is a digital direct current null circuit 34. To conveniently center the eddy current signal at zero so that it appears at the center of a display, the direct current value of the eddy current signal, which is stored in a reference memory 36, is subtracted from all signals that follow. The direct current reference signal is one of the outputs of the decimating low-pass filters 32. With the eddy current signal thus demodulated from the carrier wave 27 and centered about zero, it is available for display and analysis.

Having described the invention, what is claimed is as follows:

1. The method of measuring anomalies, or defects, in a test material proximate one or more coils of an eddy current probe, comprising the following steps:
   a. in an electrical circuit, synthesizing a digital carrier signal and digital functions;
   b. converting the digital carrier signal to an analog carrier signal;
   c. driving a probe test coil in an eddy current probe with the analog carrier signal therein generating a probe electromagnetic field from the probe test coil into the proximate test material which excites eddy currents in the test material that cause a return electromagnetic wave generally out of phase with the probe electromagnetic wave;
   d. passing the probe test coil over a material anomaly, or material defect, the anomaly causing amplitude and phase differences in said return electromagnetic wave, which wave causes an electric current in the probe test coil to vary as a modulation of the return electromagnetic wave, the phase differences, or equivalently frequency changes, constituting an eddy current signature of the anomaly;
   e. receiving said return electromagnetic wave in a probe detection coil causing an electrical analog carrier signal within the coil;
   f. amplifying the analog carrier signal;
   g. digitizing said analog carrier signal into a digital carrier signal;
   h. mixing said digital carrier signal with said digital functions;
   i. isolating the eddy current signature of the anomaly by filtering said mixed digital carrier signal with a low-pass filter.

2. The method of claim 1 wherein the digital functions comprise a mathematically complete orthogonal set.

3. The method of claim 2 wherein the digital functions are sine and cosine functions.

4. The method of claim 3 further comprising the step of separating the eddy current signal from extraneous signals after the step of mixing said digital carrier signal with said digital functions.

5. The method of claim 1 wherein the step of mixing said digital carrier signal with said digital functions further comprises the step of rejecting all but difference frequencies between the digital carrier signal and the digital functions, which difference frequencies comprise the eddy current signature demodulated from the digital carrier signal.

6. The method of claim 5 wherein the step of rejecting all but difference frequencies further comprises translating frequencies in the digital carrier signal to lower frequencies.

7. The method of claim 1 wherein the step of mixing said digital carrier signal with said digital functions comprises mathematically multiplying said digital carrier signal by said digital functions digitally in a mixer, producing only sum and difference frequency signals without harmonics of the mixed digital carrier signal.

8. The method of claim 7 wherein said digital functions are sine and cosine functions.

9. The method of claim 1 further comprising the step of translating the eddy current signature after the step of mixing said digital carrier signal with said digital functions.

10. The method of claim 9 wherein the step of translating the eddy current signature comprises the step of subtracting a reference component.

11. The method of claim 10 wherein the step of separating the eddy current signal from extraneous signals includes the step of applying a digital low pass frequency filter.

12. The method of claim 10 wherein the step of subtracting a reference component further comprises the step of subtracting a direct current component of the eddy current signal.

13. The method of claim 12 wherein the step of subtracting a direct current component of the eddy current signal includes the step of storing said direct current component of the eddy current signal in a reference memory for later extraction as said reference component.

14. The method of measuring anomalies, or defects, in a test material proximate one or more coils of an eddy current probe, comprising the following steps:
   a. in an electric circuit, synthesizing a digital carrier signal and digital sine and cosine functions;
   b. converting the digital carrier signal to an analog carrier signal;
   c. driving a probe test coil in an eddy current probe with the analog carrier signal therein generating a probe electromagnetic field from the probe test coil into the proximate test material which excites eddy currents in the test material that cause a return electromagnetic field generally out of phase with the probe electromagnetic field;
   d. passing the probe test coil over a material anomaly, or material defect, the anomaly causing amplitude and phase differences in said return electromagnetic wave, which wave causes an electric current in the probe test coil to vary as a modulation of the return electromagnetic wave, the phase differences, or equivalently frequency changes, constituting an eddy current signature of the anomaly.
   e. receiving said return electromagnetic wave in a probe detection coil causing an electrical analog carrier signal within the coil;
   f. amplifying the analog carrier signal;
   g. digitizing said analog carrier signal into a digital carrier signal;
   h. mathematically multiplying said digital carrier signal digitally by said digital sine and cosine functions in a mixer that produces only sum and difference frequency signals without harmonics of the mixed digital carrier signal;

i. passing said mixed digital carrier signal through a low-pass filter functionally isolating the eddy current signature of the anomaly thereby rejecting all but difference frequencies between the digital carrier signal and the digital functions, which difference frequencies comprise the eddy current signature demodulated from the digital carrier signal.

j. subtracting a direct current reference component of the eddy current signature from the eddy current signature, the reference component having been extracted from a prior eddy current signature and stored in a reference memory for later application as said reference component.

15. The method of claim 14 further comprising the step of translating the eddy current signature alter the step of mixing said digital carrier signal with said digital functions.

16. The method of claim 14 further comprising the step of separating the eddy current signal from extraneous signals after the step of mixing said digital carrier signal with said digital functions.

17. An electrical circuit operationally generating and digitally demodulating an electrical eddy current signature derived from defects in a material proximate one or more eddy current coils of an eddy current probe, said electrical circuit comprising:

a. a signal synthesizer operationally generating a digital carrier signal and digital sine and cosine functions;

b. a digital to analog converter electrically converting the digital carrier generated by the signal synthesizer to an analog carrier signal, the digital to analog converter electrically communicating with the probe test coil to drive it to generate an electromagnetic carrier wave into said test material, therein generating eddy currents from material defects found in the material by the carrier wave, the eddy currents producing an electromagnetic return wave detected by said probe coils, an electrical return analog carrier signal generated in the probe coils;

c. an amplifier electrically amplifying said the analog carrier signal;

d. an analog to digital converter converting said analog carrier signal into a digital carrier signal;

e. a mixer mathematically multiplying said digital carrier signal digitally by said digital sine and cosine functions producing only sum and difference frequency signals without harmonics of the mixed digital carrier signal;

f. a digital low-pass filter through which said mixed digital carrier signal passes, therein operationally rejecting all but difference frequencies between the carrier signal and the digital functions in filtering said mixed digital signal, which difference frequencies comprise the eddy current signature demodulated from the digital carrier signal, thereby functionally digitally isolating the eddy current signature;

g. a reference memory in which a prior eddy current signature is stored for later application as a direct current reference component, said reference component being electrically extractable from said reference memory for subtraction from said eddy current signature.

* * * * *